US012679976B2

(12) United States Patent
Wu et al.

(10) Patent No.: US 12,679,976 B2
(45) Date of Patent: Jul. 14, 2026

(54) TRIBOELECTRIC NANOGENERATOR

(71) Applicant: Purdue Research Foundation, West Lafayette, IN (US)

(72) Inventors: Wenzhuo Wu, West Lafayette, IN (US); Ruoxing Wang, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 1207 days.

(21) Appl. No.: 17/190,464

(22) Filed: Mar. 3, 2021

(65) Prior Publication Data

US 2021/0351720 A1      Nov. 11, 2021

Related U.S. Application Data

(60) Provisional application No. 63/021,143, filed on May 7, 2020.

(51) Int. Cl.
| | |
|---|---|
| *C08L 89/06* | (2006.01) |
| *C08L 29/04* | (2006.01) |
| *A61B 5/00* | (2006.01) |
| *A61B 5/024* | (2006.01) |
| *A61B 5/026* | (2006.01) |

(52) U.S. Cl.
CPC .............. *C08L 89/06* (2013.01); *C08L 29/04* (2013.01); *A61B 5/02405* (2013.01); *A61B 5/02416* (2013.01); *A61B 5/0261* (2013.01); *A61B 5/6824* (2013.01); *A61B 5/6832* (2013.01); *A61B 2560/0214* (2013.01); *A61B 2562/0285* (2013.01); *C08L 2203/02* (2013.01); *C08L 2203/20* (2013.01)

(58) Field of Classification Search
CPC ...... C08L 89/06; C08L 29/04; C08L 2203/02; C08L 2203/20
See application file for complete search history.

(56) References Cited

U.S. PATENT DOCUMENTS

| | | | | |
|---|---|---|---|---|
| 8,034,362 | B2 * | 10/2011 | Thomas .................. | A61L 27/26 |
| | | | | 525/50 |
| 2007/0054990 | A1 | 3/2007 | Ruberti et al. | |

| | | | | |
|---|---|---|---|---|
| 2009/0312462 | A1 * | 12/2009 | Oakley .................. | B29C 48/21 |
| | | | | 524/47 |
| 2015/0061464 | A1 | 3/2015 | Park et al. | |
| 2016/0036351 | A1 | 2/2016 | Kim et al. | |
| 2017/0054067 | A1 | 2/2017 | Zhang et al. | |
| 2021/0351720 | A1 | 11/2021 | Wu et al. | |

FOREIGN PATENT DOCUMENTS

| | | | | | |
|---|---|---|---|---|---|
| RU | | 2592117 C1 * | 7/2016 | ............... | G03C 1/00 |

OTHER PUBLICATIONS

Clarivate Analytics machine translation of RU 2592117 C1 published Jul. 20, 2016. (Year: 2016).*
Guan et al. Journal of Materials Chemistry A, 2019, 7, 13948. Published online Apr. 8, 2019. (Year: 2019).*
Pawde et al. Journal of Applied Polymer Science, 2008, vol. 109, 3431-3437. Published online May 27, 2008 (Year: 2008).*
Liu et al. Journal of the Mechanical Behavior of Biomedical Materials, 3, 2010, 203-209. Published online Jul. 14, 2009. (Year: 2009).*
Xu et al. Advanced Energy Materials, 2017, 7, 1601529. Published online Sep. 16, 2016 (Year: 2016).*
Choudhury et al. Journal of The Electrochemical Society, 155, 1, A74-A81 (2008). Published online Nov. 15, 2007. (Year: 2007).*
Acar et al. Advanced Functional Materials, 2014, 24, 4135-4143. Published online Apr. 1, 2014 (Year: 2014).*
International Search Report for International Application No. PCT/US2021/020570, dated May 19, 2021, (3 pages).
Wang, R. et al., (Manuscript)—Holistically Engineered Polymer-Polymer and Polymer-ion Interactions in Biocompatible Polyvinyl Alcohol Blends for High-Performance Triboelectric Devices in Self-Powered Wearable Cardiovascular Monitoring, (19 pages).

* cited by examiner

*Primary Examiner* — Jane L Stanley

(74) *Attorney, Agent, or Firm* — Purdue Research Foundation

(57) ABSTRACT

The present disclosure relates to a novel triboelectric nanogenerator comprising a novel polyvinyl alcohol (PVA)-based biocompatible polymer. The novel polyvinyl alcohol-based biocompatible polymer comprises a blending product of a mixture comprising a polyvinyl alcohol, a gelatin, and an optional salt. The polyvinyl alcohol-based biocompatible polymer is a substantially transparent film.

12 Claims, 5 Drawing Sheets

TRIBOELECTRIC NANOGENERATOR

CROSS-REFERENCE TO RELATED APPLICATIONS

This application claims the benefit of U.S. Provisional Application No. 63/021,143 filed May 7, 2020, the entirety of which is incorporated by reference herein.

GOVERNMENT RIGHTS

This invention was made with government support under Award No. CBET-1603264 awarded by the National Science Foundation (NSF). The government has certain rights in the invention.

TECHNICAL FIELD

The present disclosure relates to a novel triboelectric nanogenerator comprising a novel polyvinyl alcohol (PVA)-based biocompatible polymer. The novel polyvinyl alcohol-based biocompatible polymer comprises a blending product of a mixture comprising a polyvinyl alcohol, a gelatin, and an optional salt.

BACKGROUND

This section introduces aspects that may help facilitate a better understanding of the disclosure. Accordingly, these statements are to be read in this light and are not to be understood as admissions about what is or is not prior art.

The emerging frontiers in personalized, on-demand diagnostics and therapeutics demand that the electronic systems be biocompatible, mechanically-deformable, and self-sustainable. The capability to efficiently scavenge the stray, weak environmental energies through sustainable pathways enables viable self-powering schemes for supporting the operations of electronics and sensors in related applications. To this end, an assortment of technologies has been demonstrated to transform the otherwise wasted mechanical energy abundant in the environment into electrical power. Among these technologies, triboelectric nanogenerators (TENG), hinged on a synergy of triboelectrification and electrostatic induction, can efficiently harvest the mechanical energy for powering electronics and sensors. Moreover, advantageous to the other technologies (e.g., piezoelectric, electromagnetic) for mechanical energy harvesting, TENGs exhibit characteristics appealing for biomedical and implanted applications, such as biocompatibility and biodegradability through material engineering. Though still in its infancy, the exploration for efficient triboelectric devices made of biocompatible materials has gained increased interests. To improve the output performance of these biocompatible triboelectric devices, which are generally not on par with the TENGs built with synthetic nondegradable polymers (e.g., Nylons, PDMS), it is critical to comprehend the interactions between the constituent materials and the impact of corresponding structure-property relations on the device performance.

Polyvinyl alcohol (PVA) is one of the most widely used polymers for biomedical applications owing to its water-solubility and biocompatibility. The pure PVA has been recently employed as a contact layer in TENGs due to its hydrophilicity, biodegradability, and biocompatibility. Nevertheless, pure PVA has relatively limited functionality and high processing cost. Meanwhile, recent reports showed that the addition of a small amount of molecules, including starch, chitosan, etc. could enable a versatile modulation of the mechanical properties and biodegradability in the formed PVA blends with improved performance and significantly reduced cost. However, a fundamental understanding of the impact of the molecular/ionic engineering for the PVA blends on their triboelectric performance has yet to be revealed. The lack of such knowledge hinders the rational design and holistic engineering for more capable triboelectric devices constructed with biocompatible materials.

Therefore, there is an unmet need for developing novel PVA blends with improved performance and significantly reduced cost for TENGs.

SUMMARY

The present disclosure relates to a novel triboelectric nanogenerator comprising a novel polyvinyl alcohol (PVA)-based biocompatible polymer. The novel polyvinyl alcohol-based biocompatible polymer comprises a blending product of a mixture comprising a polyvinyl alcohol, a gelatin, and an optional salt.

In one embodiment, the present disclosure provides a triboelectric nanogenerator comprising a polyvinyl alcohol (PVA)-based biocompatible polymer, wherein the polyvinyl alcohol-based biocompatible polymer comprises a blending product of a mixture comprising a polyvinyl alcohol, a gelatin, and an optional salt.

DETAILED DESCRIPTION

Figure 1:
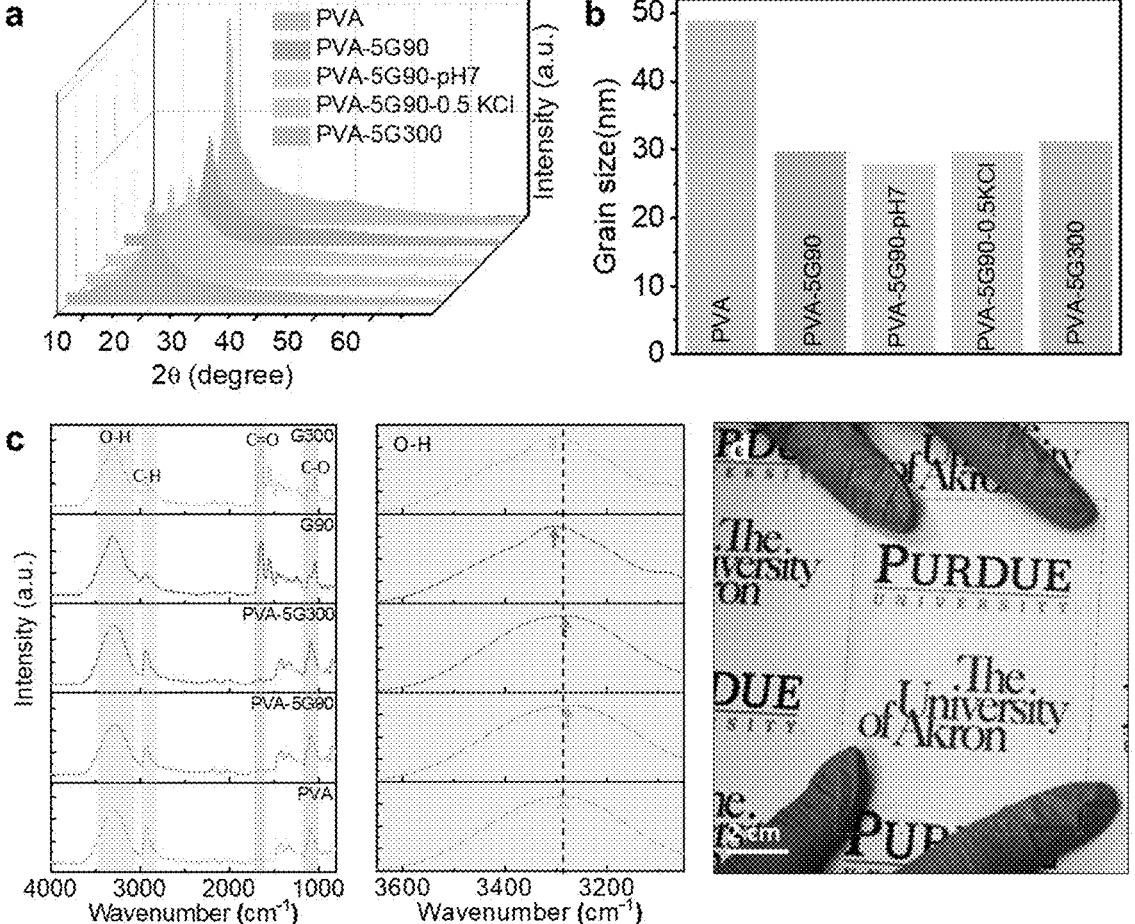
FIG. 1 illustrates PVA and PVA blends characterizations. (a) XRD patterns of PVA and PVA blends. (b) Grain sizes from the FWHM in XRD patterns. (c) IR spectra of PVA, gelatin, and PVA-gelatin blends. The enlarged IR peaks within 3000-3600 $cm^{-1}$ represent the hydroxyl groups. (d) The optical image of PVA-5G90 film.

For the purposes of promoting an understanding of the principles of the present disclosure, reference will now be made to embodiments illustrated in drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

In the present disclosure the term "blend" may be a physical blending or may include chemical reactions between the blended mixtures.

This disclosure provides a profound understanding of the impact of the molecular/ionic fillers on PVA blends' triboelectric performance through systematic material engineering and characterization of PVA blends at different structure levels. Three types of fillers, namely gelatin, HCl/NaOH, and KCl/NaCl, were selected to study the influences of factors such as molecules, pH values, and ions, respectively. These filler materials are readily accessible. More importantly, their abundant functional groups/ions can form hydrogen bonds or complexation with PVA molecules, which induces process-controlled interfacial polarization and ionic polarization in the formed PVA blends. Subsequently, the dielectric constant, which is directly related to TENG outputs, can be engineered by enhancing or limiting the mobility of the polarized groups in PVA blends. The demonstrated strategies for molecular/ionic engineering using cost-effective, accessible fillers enables the modulation of the energy harvesting performances of PVA films. The optimized PVA-gelatin blended film shows stable and robust electricity outputs as well as low detection limits of mechanical deformation such as human pulse. Leveraging the advantages such as flexibility and biocompatibility, the PVA-blends based triboelectric devices show exciting potential for cost-effective human health monitoring and offer new strategies for designing future biocompatible TENG.

In one embodiment, the present disclosure provides a triboelectric nanogenerator comprising a polyvinyl alcohol (PVA)-based biocompatible polymer, wherein the polyvinyl alcohol-based biocompatible polymer comprises a blending product of a mixture comprising a polyvinyl alcohol, a gelatin, and an optional salt.

In one embodiment regarding the triboelectric nanogenerator of the present disclosure, wherein the polyvinyl alcohol (PVA)-based biocompatible polymer comprises a blending product of a mixture comprising a polyvinyl alcohol, a gelatin, and a salt, wherein the salt comprises NaCl, KCl, or a combination thereof. In one aspect, the weight percentage of the salt is 0.1-1.5 wt. % of the total weight of the polyvinyl alcohol (PVA)-based biocompatible polymer.

In one embodiment regarding the triboelectric nanogenerator of the present disclosure, wherein the polyvinyl alcohol (PVA)-based biocompatible polymer has 1-20, 1-15, or 1-10 wt. % gelatin.

In one embodiment regarding the triboelectric nanogenerator of the present disclosure, wherein the polyvinyl alcohol (PVA)-based biocompatible polymer is a substantially transparent film.

In one embodiment regarding the triboelectric nanogenerator of the present disclosure, wherein the molecular weight of said polyvinyl alcohol is 100,000 to 250,000, the molecular weight of said gelatin is 10,000 to 150,000.

In one embodiment regarding the triboelectric nanogenerator of the present disclosure, wherein the triboelectric nanogenerator further comprises a friction layer as a counter part of the polyvinyl alcohol (PVA)-based biocompatible polymer, wherein the polyvinyl alcohol (PVA)-based biocompatible polymer and the friction layer are backed by metal electrodes, and when the polyvinyl alcohol (PVA)-based biocompatible polymer is brought into contact with the friction layer, the difference from triboelectric polarities on the polyvinyl alcohol (PVA)-based biocompatible polymer and the friction layer leads to electrons flowing between the polyvinyl alcohol (PVA)-based biocompatible polymer and the friction layer. In one aspect, the friction layer can be any appropriate polymeric or metal materials. In one aspect, the friction layer may be but is not limited to Kapton (polyimide), Polytetrafluoroethylene (PTFE), Polydimethylsiloxane (PDMS), Polyvinyl chloride (PVC), Polypropylene (PP), or a metal.

In one embodiment regarding the triboelectric nanogenerator of the present disclosure, wherein the polyvinyl alcohol (PVA)-based biocompatible polymer is prepared as a neutral material with pH range of 6.5-7.5. In one aspect, pH is about 7.

In one embodiment regarding the triboelectric nanogenerator of the present disclosure, wherein the polyvinyl alcohol (PVA)-based biocompatible polymer has dielectric constant range of 8-20.

In one embodiment, the present disclosure provides a polyvinyl alcohol (PVA)-based biocompatible polymer, wherein the polyvinyl alcohol-based biocompatible polymer comprises a blending product of a mixture comprising a polyvinyl alcohol, a gelatin, and an optional salt.

In one embodiment regarding the polyvinyl alcohol (PVA)-based biocompatible polymer of the present disclosure, wherein the polyvinyl alcohol (PVA)-based biocompatible polymer comprises a blending product of a mixture comprising a polyvinyl alcohol, a gelatin, and a salt, wherein the salt comprises NaCl, KCl, or a combination thereof, and wherein the weight percentage of the salt is 0.1-1.5 wt. % of the total weight of the polyvinyl alcohol (PVA)-based biocompatible polymer.

In one embodiment regarding the polyvinyl alcohol (PVA)-based biocompatible polymer of the present disclosure, wherein the polyvinyl alcohol (PVA)-based biocompatible polymer has 1-20 wt. % of gelatin.

In one embodiment regarding the polyvinyl alcohol (PVA)-based biocompatible polymer of the present disclosure, wherein the salt contributes to 0.1-1.0 wt. % of the total weight of the polyvinyl alcohol (PVA)-based biocompatible polymer, and the gelatin contributes to 1-10 wt. % of the total weight of the polyvinyl alcohol (PVA)-based biocompatible polymer.

In one embodiment regarding the polyvinyl alcohol (PVA)-based biocompatible polymer of the present disclosure, wherein the polyvinyl alcohol (PVA)-based biocompatible polymer has dielectric constant range of 8-20.

In one embodiment regarding the polyvinyl alcohol (PVA)-based biocompatible polymer of the present disclosure, wherein the polyvinyl alcohol (PVA)-based biocompatible polymer is prepared as a neutral material with pH range of 6.5-7.5. In one aspect, pH is about 7.

Methods

Materials. Gelatin from porcine skin (G90: 90-110 g bloom, Mw=20,000~25,000; G300: 300 g bloom, Mw=50,000~100,000), sodium chloride (NaCl, ≥99.5%), potassium chloride (KCl, ≥99.0%), sodium hydroxide (NaOH, ≥98.0%), hydrochloric acid (HCl, 37%) and Poly(vinyl alcohol) (PVA, Mw=146,000~186,000, 99% hydrolyzed) were purchased from Sigma-Aldrich. Deionized water was purified using a Milli-Q Direct 8 Ultrapure Water system (Millipore, Billerica, MA) with minimum resistivity of 18.2 MΩ·cm. All chemicals were used as received without further treatment.

Materials Preparation. 3.0 g PVA was firstly dissolved in 27 g DI water and mechanically stirred at 90° C. for 12 hours to prepare 10 wt % PVA aqueous solutions. Then, an appropriate amount of G90, G300, and NaCl/KCl was dissolved in 30 g DI water and added in the PVA solution. The weight ratio of G90 and G300 in the aqueous solution was controlled at 2, 5, 7, and 10 wt %, and the weight ratio of NaCl/KCl was fixed at 0.5, 0.9 and 1.3 wt %. The mixture was continuously stirred at 90° C. for 6 hours to obtain a homogeneous solution. Then, the solution was blade-casted and dried at 50° C. for 24 hours. Finally, the blending films (PVA-gelatin, PVA-5G90-NaCl, PVA-5G90-KCl) were peeled off from the glass plate and kept in the ambient environment for 7 days at a relative humidity of 50% before testing. The PVA-gelatin samples were named as "PVA-n X" where n represents the weight percentage, and X represents the G90 or G300. The PVA-G90-KCl or PVA-G90-NaCl samples were donated as "PVA-5G90-mY" where m represents the weight percentage, and Y represents the NaCl or KCl. To study the effect of pH on the TENG output efficiency, the pH value (5, 7, 9) of PVA-5G90 solution was adjusted via the HCl and NaOH. Accordingly, these PVA-5G90 blends at the different pH were named as PVA-5G90-pH5, PVA-5G90-pH7, PVA-5G90-pH9.

Characterization. Fourier transform infrared-attenuated total reflection (FT-IR-ATR) spectra were recorded with a Thermo Scientific Nicolet 380 series spectrometer. The PVA, PVA-gelatin, PVA-G90-NaCl, PVA-gelatin-KCl and PVA-G90-pH5/7/9 aqueous solutions were diluted 60 times, and then their hydrodynamic diameters were measured with a Zetasizer Nano ZS Malvern dynamic light scattering (DLS) instrument, operating at a wavelength of 633 nm and a scattering angle of 173 at 25° C. The dispersant refractive index and the viscosity of water were taken as 1.330 and 0.8872 cP, respectively. The powder X-ray diffraction was used to analyze the crystals in the composite film by using a Bruker AXS D8 Discover diffractometer with GADDS (General Area Detector Diffraction System) operating with a Cu—K α radiation source filtered with a graphite monochromator ($\lambda$=1.541 Å). A linear motor (LinMot PS01-23× 80) was used for applying programmed strain (operating distance, 20 mm; maximum speed, 1 m/s; acceleration, 1 m/s$^2$; deceleration, 1 m/s$^2$). Electrical measurements were taken on an electrometer (Keithley 6514) and a low current preamplifier (Stanford Research System, SR570).

Results and Discussion

The presence of molecules or ions, even in small amounts, could dramatically affect the physical and chemical properties of PVA blends. To study the impacts of added fillers on the PVA properties and TENG applications, PVA blends were prepared using gelatin, KCl, or NaCl as the fillers. Gelatin is a biocompatible protein product derived from collagen with abundant functional groups, such as —NH$_2$ and —C═O. Adding KCl or NaCl in PVA increases the charge of the blends since cation/anion dissociation occurs with the presence of complexation between —OH (PVA) and cations, which could influence the PVA blends' triboelectric performances. Also, both KCl and NaCl are two essential electrolytes in the human body and thus may be directly used in future human health monitoring applications. X-Ray diffraction (XRD), and Fourier-transform infrared spectroscopy (FTIR) characterizations were first performed (FIG. 1. a-c) to investigate the structural changes in PVA blends due to the additions of molecules or ions. The PVA blend samples were named following the notation "PVA-nX", where n is an integer that represents the weight percentage number for gelatin, and X indicates the gelatin from porcine skin with different gel strength (G90: 90-110 g Bloom; G300: 300 g Bloom). In FIG. 1a shows the XRD spectra of pure PVA and PVA blends. The intense peak at 19.8° is from the crystallized domains of PVA due to the self-association of hydroxyl groups. The peak intensity of pure PVA is higher than that for all the PVA blend films, implying the higher crystallinity of pure PVA. The gelatin molecules are abundant in proton donating groups (e.g., —NH$_2$) and proton accepting groups (e.g., —C═O). The existence of these groups will interfere with the compact packing of the H-bonding network among PVA chains and thus lead to a lower crystallinity in the PVA blends compared with pure PVA. The grain sizes of PVA blends, derived from the XRD results, are smaller than that of pure PVA (FIG. 1b), which is likely due to the breakage of the PVA crystalline regions via the introduction of gelatin moiety in the PVA blends.

FT-IR was used to analyze the intermolecular interactions in the PVA films (FIG. 1c). The peaks at 3300, 2925, and 1051 cm$^{-1}$ are attributed to the O—H, C—H, and C—O stretching vibrations of PVA, respectively. Gelatin has its signature peak of the C═O stretching peak at ~1635 cm$^{-1}$[52]. The shift in O—H peak can be attributed to the change of intermolecular interactions between gelatin molecules and polymer chain. Compared with pure PVA, OH peak shift was not evident in PVA-5G90 and PVA-5G300, indicating that the intensity of the newly formed H-bond interaction between gelatin and PVA is about the same as PVA-PVA interaction. It is worth mentioning that all the PVA blends show excellent transparency (e.g., PVA-5G90 in FIG. 1d), which may enable unique applications such as self-powered wearable touch interface.

Figure 2:
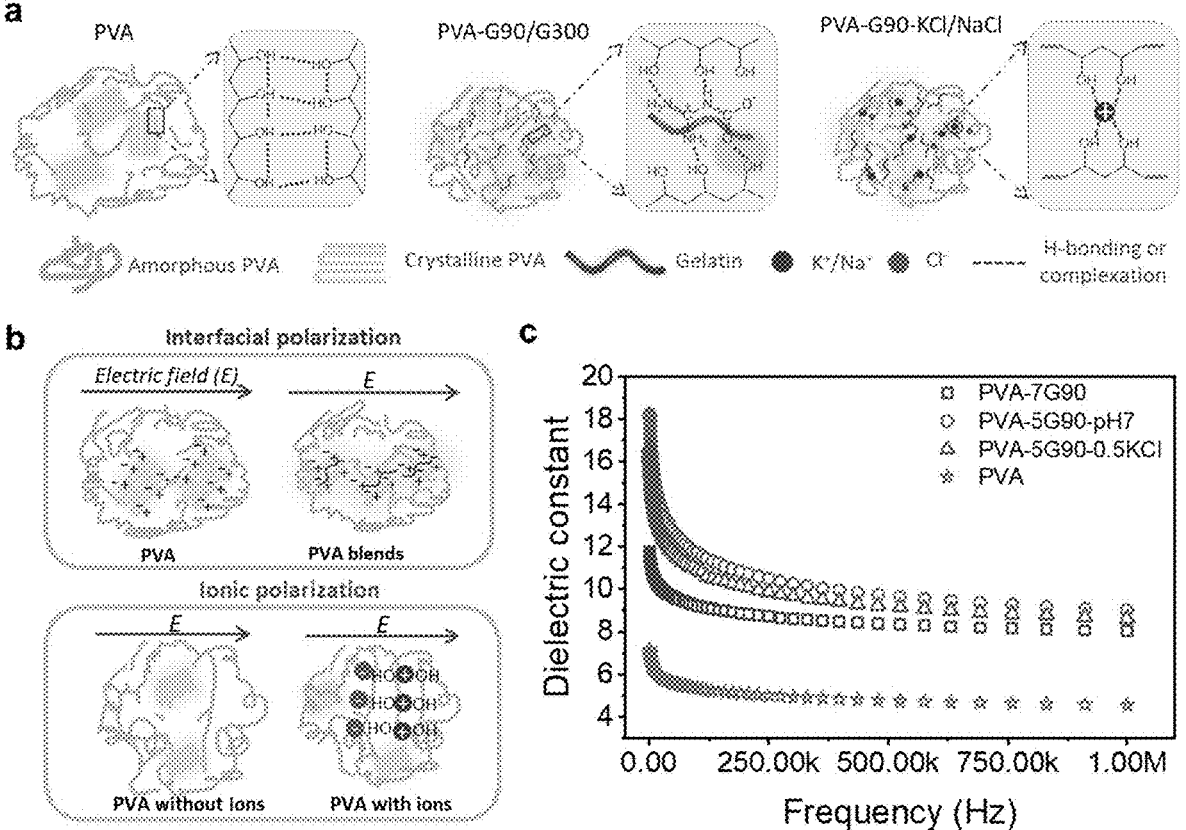
FIG. 2 illustrates (a) The schemes of interactions between PVA and different fillers. (b) The schemes of interfacial polarization and ionic polarization. (c) The measured dielectric constants of PVA and PVA blends.

Engineering the dielectric properties of triboelectric materials has been demonstrated as an effective approach to improve the triboelectric performance. Materials with higher dielectric constants are often desired since they can transfer more electrostatic charges generated from triboelectrification. Four polarization mechanisms can be applied for interface design in polymer composites, namely electronic polarization, interfacial polarization, dipolar polarization, and ionic polarization. Electronic polarization and dipolar polarization initially exist in PVA. Therefore, the interfacial polarization and ionic polarization, which are induced by the added fillers, were mainly focused. Due to the presence of abundant hydroxyl group in the PVA chains, dense H-bonds are formed which limit the mobility of the polarized groups and hinder the reorientation ability of the PVA chains (FIG. 2a). This process would decrease the dielectric constant and thus reduce the electrostatic induction efficiency of the PVA blends. Thus, pure PVA has the smallest measured dielectric constant compared with PVA blends in FIG. 2c. Due to the different electron cloud density between crystalline and amorphous regions, interfacial polarization would occur at the boundary of crystalline and amorphous regions (FIG. 2, a-b). With similar crystallinity, smaller grain size means a larger interface area, which is beneficial to increase interfacial polarization and induce greater dielectric constant (the black square scatters in (FIG. 2c). The dielectric constant is also affected by ionic polarization, which often occurs in ionic crystals such as NaCl and KCl with an applied electric field. The ions can be displaced by the electric field, leading to an enhanced polarization and, eventually, an increased dielectric constant. Also, Na$^+$ or K$^+$ ions tend to form complexation with hydroxyl groups in PVA chains (FIG. 2, a-b), which could breakdown the dense H-bonds in the PVA chains. Such a complexation process would enhance the mobility of polarized groups in PVA and increase the reorientation ability of the PVA chain when an electric field is applied. Consequently, the dielectric constant of the PVA blends is increased (FIG. 2, b-c). The pH7 sample adjusted by NaOH has similar ionic polarization due to the addition of Nat Thus, the measured dielectric constant of PVA-5G90-pH7 is higher than that of PVA in FIG. 2c. Meanwhile, the intramolecular proton transfer between carboxylic and amine groups in PVA blends will lead to separated positive/negative charges in gelatin. These charges could further increase the ionic polarization in the PVA-gelatin system. Hence, both interfacial and ionic polarizations (FIG. 2b) can be engineered for modulating the dielectric properties of triboelectric materials. The measured dielectric constants of PVA and representative blends are shown in FIG. 2c. The dielectric constants of PVA blends are larger than that of pure PVA, which is mainly attributed to the interfacial polarization and ionic polarization with the addition of gelatin or NaCl/KCl, as described above.

Figure 3:
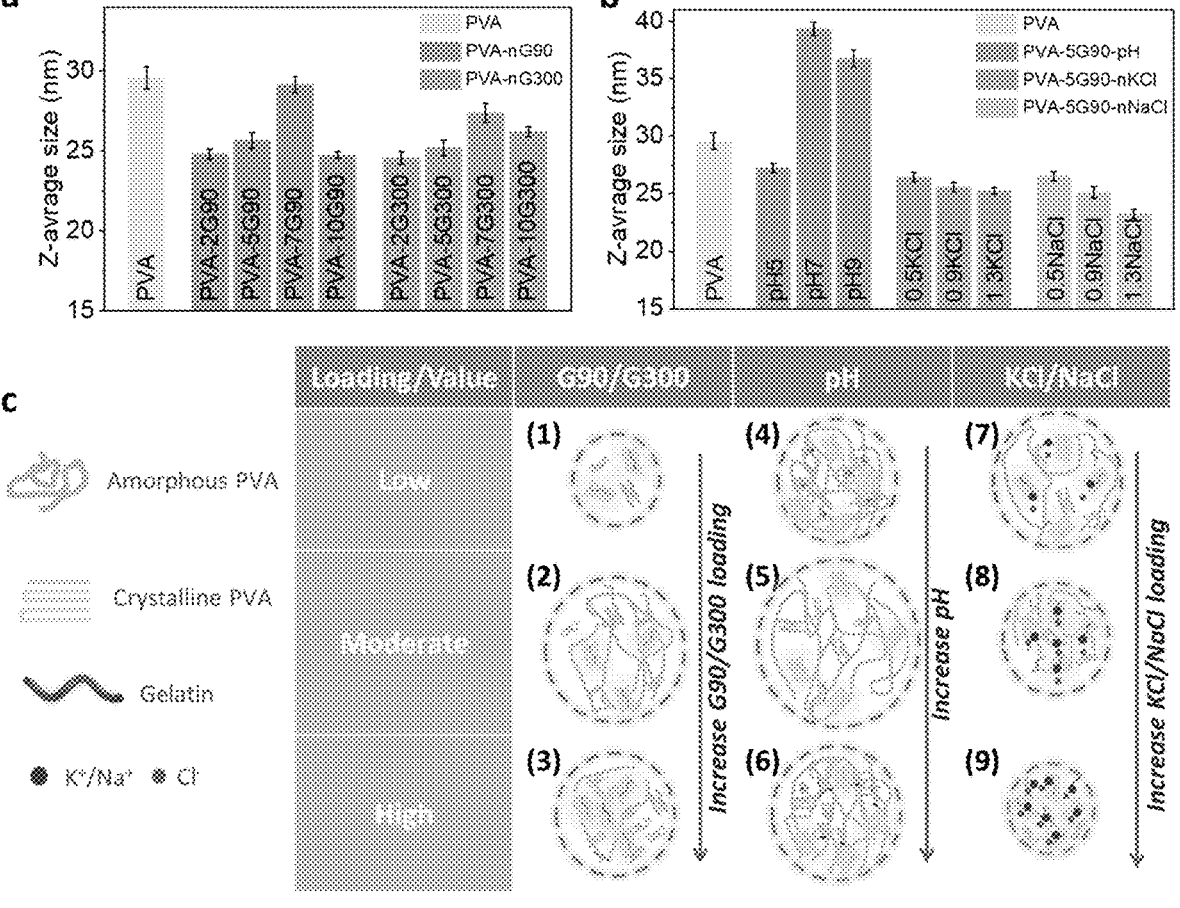
FIG. 3 illustrates Z-average sizes of (a) PVA-gelatin blends and (b) PVA blends with different pH values or ions from DLS results. (c) The table of coil conformation at the different gelatin concentration, pH value or ions loading.

Dipolar reorientation is another essential origin for the dielectric response in polymers. The dipolar reorientation ability of polymer composites is closely related to their conformation. A loose polymer conformation gives rise to a large interchain spacing, which reduces the barriers for dipole reorientation in the applied electric field and leads to a high dielectric constant. Dynamic light scattering (DLS) is widely used to probe the polymer conformation. It can reveal the coil size via the Z-average size of polymer composites by optically detecting the Brownian molecular motion of polymer composites in diluted solution. Different from the XRD results in FIG. 1b showing the grain sizes, the coil sizes measured by DLS relate to higher-level grain-containing structures. In general, the statistical dimension of polymer coils in the solvent depends on the molecular weight and concentration of the polymer, various fillers in the solution, temperature, and polymer-solvent interaction. The increase in the polymer coil size indicates a conformational transition from compact and crumbled coils to loose ones. The statistical dimensions for the coil size of the investigated PVA blends are summarized in FIG. 3, a-b. Here, by examining the changes in the average dimension size due to different fillers, it has been found that the introduction of gelatin, salts (KCl or NaCl), or pH variations can significantly affect the PVA coil size through different mechanisms, which will be elaborated in the following sections.

The coil size of PVA-G90 or PVA-G300 with different gelatin weight percentages is smaller than that of pure PVA. When the gelatin concentrations in the PVA blends (i.e., PVA-nG90 or PVA-nG300) increase (i.e., n increases), the coil size increases and reaches the highest value when the gelatin concentration is 7 wt % (FIG. 3a). Polymer coil size mostly depends on its molecular weight and the H-bonding interaction between adjacent chains. As the gelatin concentration increases, the PVA/gelatin system favors the multi-chain association through the formation of H-bonding, which leads to an increased coil size when the gelatin concentration is moderate (case (2) in FIG. 3c). Meanwhile, the polymer coil size gyration is proportional to its molecular weight ($D_Z \propto M^Z$, $D_Z$: Z-average coil size; M: molecular weight; Z: constant, <1). As a result, the polymer coil size will decrease with a reduced molecular weight of the polymer. In the system of the present disclosure, gelatin has a smaller coil size due to its smaller molecular weight than that of PVA. Therefore, the addition of gelatin at a high concentration will eventually reduce the coil size of the PVA blends (case (3) in FIG. 3c). As the concentration of the salt (NaCl or KCl) increases, the coil sizes of PVA blends decrease accordingly (FIG. 3b). Such a change is because the complexation between $K^+/Na^+$ and the hydroxyl groups in PVA can lead to the formation of dense PVA chain entanglements and hence a reduced polymer coil size (from case (7) to case (9) in FIG. 3c). As for the effect of pH on the coil size, the largest coil size occurs at pH=7 (FIG. 3b and case (5) in FIG. 3c). Smaller coil size is observed at higher or lower pH conditions. The smaller coil size of PVA-5G90-pH5 in case (4), compared to that for PVA-5G90-pH7/9, is likely due to the protonation of amino groups in gelatin in acidic conditions, which induces a strong electrostatic attraction between $-NH_2^+$ in gelatin and $-OH$ in PVA. While in the basic condition, the ionization of carboxyl groups in gelatin generates an electrostatic repulsive force that stretches polymer chains to larger dimensions (i.e., larger coil sizes). On the contrary, the complexation between the cation (Nat) and $-OH$ in PVA reduces the polymer coil size. Therefore, both the electrostatic repulsive force and the complexation effect come into play in determining the coil size of PVA-5G90-pH9 (case (6) in FIG. 3c). It seems that the complexation effect is the dominating factor in this case, as PVA-5G90-pH9 shows a relatively smaller coil size than that of PVA-5G90-pH7.

Figure 4:
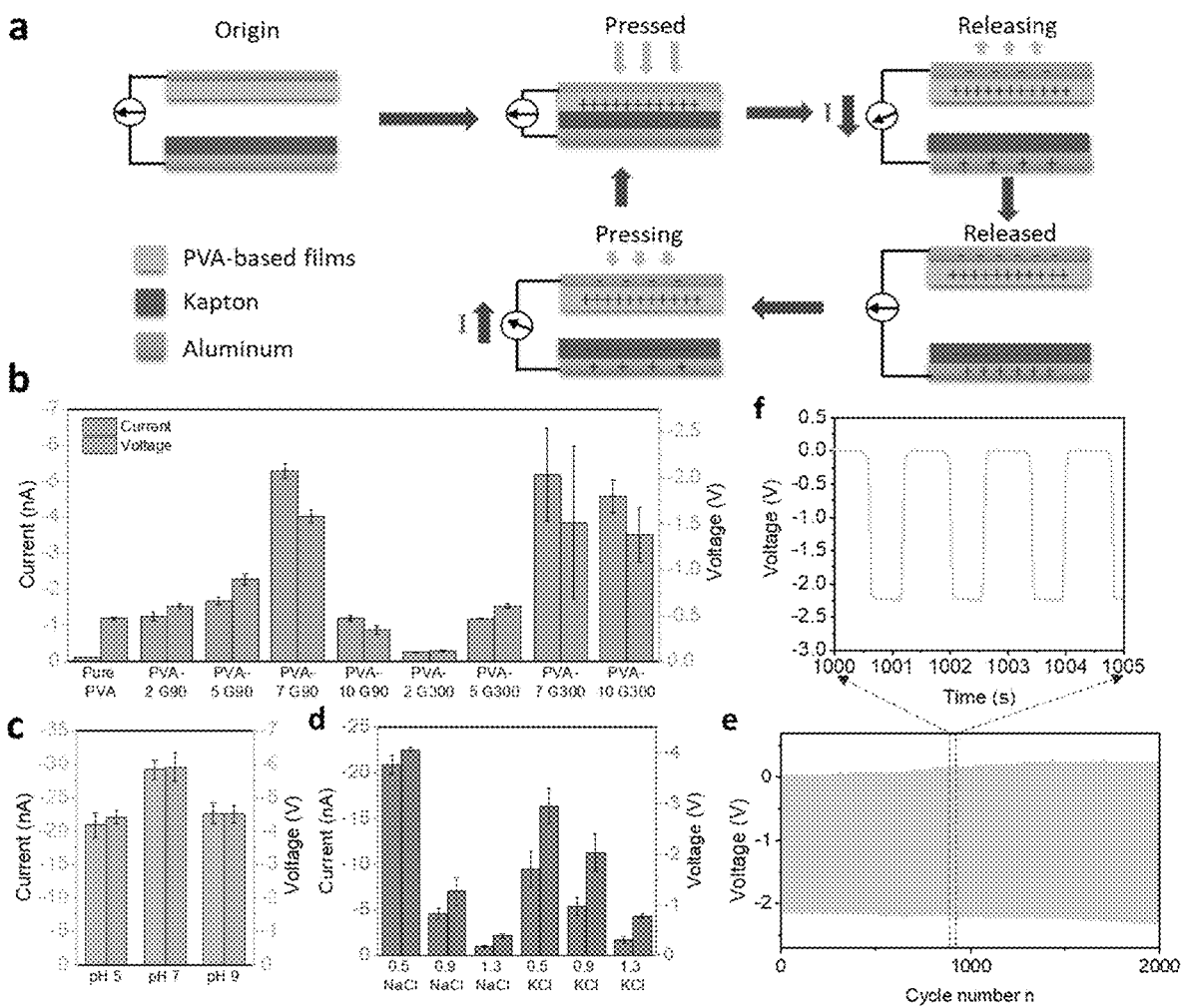
FIG. 4 illustrates (a) Schematic diagram of the working mechanism of PVA-based TENG. (b-d) Summarized currents and voltages outputs of PVA-based TENGs. (e) The stability test of PVA-7 G90 sample. (f) The magnified cycles from the blue box in (e).

To further explore the effects of fillers and ions on triboelectric energy harvesting performance, the as-prepared PVA-based films were fabricated into TENGs. The typical structure of PVA-based TENG is shown in FIG. 4a, including the friction layers and the electrodes. A PVA-based film and a Kapton film were assembled as the friction layers, both with aluminum electrodes attached on the back. The Kapton film was driven by a linear motor to contact and separate from the PVA-based films. An alternating flow of electrons between electrodes was generated by coupling the triboelectrification and electrostatic induction, which is strongly dependent on the composition and preparation of the composites. Kapton is located at the negative side in the triboelectric series, which is far away from the location of PVA (positive) in the same series. Thus, Kapton will gain electrons (becoming negatively charged) when contacted with PVA. In a typical case, electrons transfer from PVA to Kapton when both layers are pressed to contact, resulting in triboelectric charges retaining on surfaces of both layers. The subsequent separation of the two films results in an electric field (and a voltage drop) between the two electrodes, which will drive the electrons to flow in the external circuit. Such flow of electrons will screen the original electric field from the triboelectric charges. The periodic contacting and releasing events would generate an output electrical power through the back-and-forth flow of electrons in the external circuit.

The output performance of PVA-based TENGs was tested and organized into three groups (elaborated below), based on their influencing mechanism described previously. The negative sign/polarity of the measured TENG outputs is consistent with the fact that the locations of PVA-based films are positive compared with that of Kapton in the triboelectric series.

(1) The first group is pure PVA mixed with different amounts or types of gelatin. When gelatin is added as the filler, both output current and voltage of the PVA-blended films increase compared with that of pure PVA film, due to the higher dielectric constants induced by the smaller grain sizes and larger interfacial polarization (FIG. 2a). Leveraging the abundant proton donating groups ($-NH_2$) and proton accepting groups ($-C=O$) in gelatin, PVA-gelatin films can form three-dimensional (3D) networks through hydrogen bonds which promote the electron transport[73]. The output signals reached the maximum for PVA-7G90 and decreased with more filler loadings, which could be attributed to the fact that the denser network was formed with a smaller coil size. More filler loadings lead to abundant H-bonds, which limit the mobility of the polarized groups and hinder the reorientation ability of PVA chains, thus decreasing the dielectric constant. Taking advantages of the appropriate 3D networks and the beneficial effect of small grain size, the PVA-7G90 film can generate 5.3 nA short-circuit current and 1.6 V open-circuit voltage with low-frequency (0.8 Hz) periodic mechanical input, which is significantly improved compared to pure PVA film based devices (FIG. 4b). With longer chain length and the same structure to gelatin 90, PVA films incorporating gelatin 300 show a similar trend to PVA films with gelatin 90 fillers. The triboelectric outputs of PVA blends with gelatin 300 increase with more filler loadings and reach a maximum with 7 wt % gelatin 300, then decrease with further addition of gelatin 300 fillers (FIG. 4b).

(2) The second group includes the PVA-based films with different pH values. In both the acidic and basic environments, unbalanced charges are free to neutralize the triboelectric charges induced on the surface of friction layers and hence attenuate the outputs. Also, the largest coil size achieved at pH7 (case (5) in FIG. 3c) allows more space for the reorientation of PVA chains and hence higher mobility of the polarized groups in PVA, resulting in a higher dielectric constant. At pH=7, the electrostatically equilibrated film exhibits the highest output of 29.2 nA and 5.9 V within this group (FIG. 4c).

(3) The third group was used to investigate the effect of $Na^+$ and $K^+$ ions, which are two common ions in our daily life, in the human body, and closely related to human health. The added ions are thought to lead to the formation of complex structures with hydroxyl groups in PVA chains, which facilitates the reorientation of PVA dipoles and increases the dielectric constant of the PVA blends. However, the high loading of these ions results in a compact network structure that decreases the TENG outputs. From the DLS results in FIG. 3b, $K^+$, which has a larger ionic radius than that of Nat, forms smaller coils with denser internal networks compared with Na at the same concentration. Consequently, the film PVA-5G90-0.5NaCl generates the highest output among this group (FIG. 4d). FIG. 4e shows the stability test of the PVA-based TENG over a period of 2000 contact-separation cycles (0.8 Hz), revealing the mechanical durability of the material and device. FIG. 4f is the enlarged plot corresponding to the cycles indicated as the blue box in FIG. 4e. The open-circuit voltages have a typical square wave shape without noticeable noise or degradation over a long period of operation.

Figure 5:
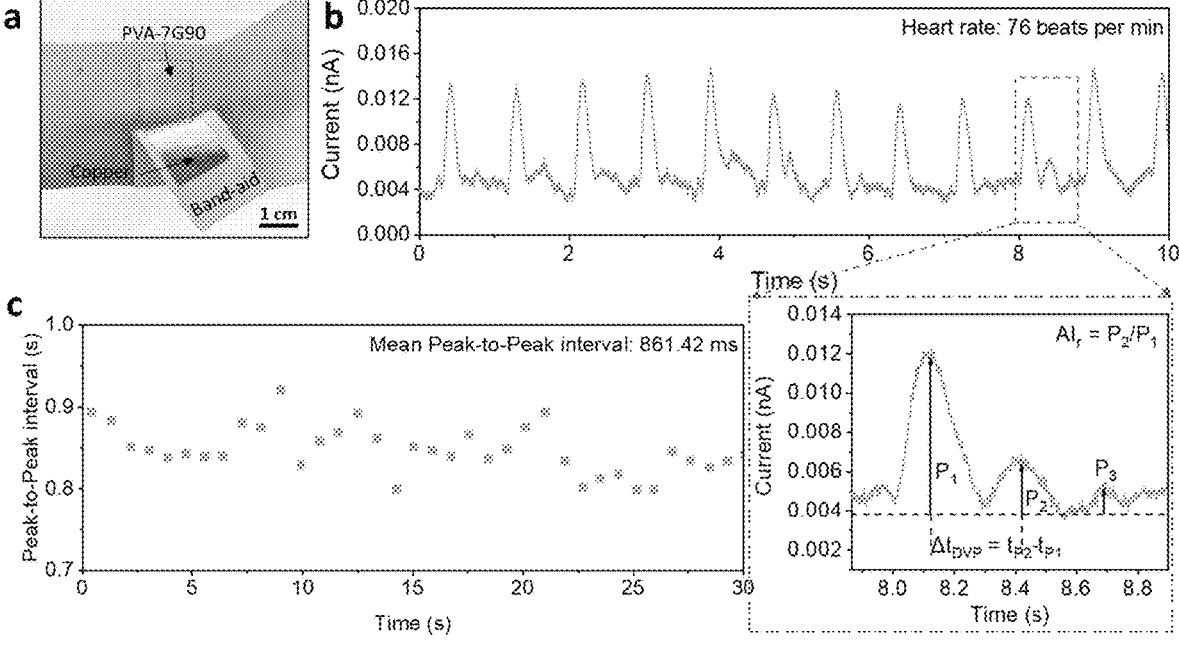
FIG. 5 illustrates (a) The optical image of the PVA-7G90 film attached on the human wrist. (b) The real-time current outputs from the PVA-based TENG device measuring the pulses. One pulse period was enlarged from (b). (c) The peak to peak intervals plot.

Leveraging the high mechanical deformability and biocompatibility of the PVA-based films, the PVA-based TENGs are capable of monitoring physiological signals vital for human health (e.g., cardiovascular monitoring, FIG. 5). The human pulse induces an imperceptible degree of deformation in the skin (corresponding pressure smaller than 0.6 $N\ cm^{-2}$), which demands a low detection limit and high sensitivity in the related mechanical sensors to capture the detailed information encoded in the pulse with high fidelity. The state-of-the-art commercial devices such as the electrocardiogram (ECG) and photoplethysmography (PPG) are limited by their high cost. Besides, the energy consumption of the devices remains a challenge for volume and weight reduction and further wearable system integration. The present disclosure has explored and demonstrated the capability of PVA-based triboelectric sensor for self-powered wearable cardiovascular monitoring. PVA-7G90 was selected for this demonstration because it has the highest output among PVA-gelatin systems without ions (FIG. 4b). FIG. 5a shows the PVA-7G90 based wearable transparent device (outlined by the red dashed lines) on a human wrist. A band-aid with copper tape was covered as the counter electrode onto the PVA film. FIG. 5b shows the real-time triboelectric current generated from the device, with three distinct characteristic peaks corresponding to the human pulse cycles. It should be noted that the measured peaks are different from those obtained from other conventional methods, such as the ECG. ECG measures the electrical activity of the heartbeat. The signals detected by device of the present disclosure are directly related to the blood flow and corresponding skin deformation, which is similar to the photoplethysmography (PPG), which monitors the changes in blood volume in a portion of the peripheral microvasculature. PVA-based triboelectric device of the present disclosure can be seamlessly worn on the human skin and generate pulse waveforms that contain detailed pulse features (FIG. 4b). The heart rate can be determined as 76 beats per minute. One of the pulse periods is magnified in FIG. 4c for further analysis and health diagnostics. The three characteristic peaks represent blood ejection, blood reflection from the lower body, and blood reflection from the closed aortic valve, respectively. The time delay between the first two peaks ($\Delta t_{DVP}$) and the radial augmentation index $AI_r=P_2/P_1$ are two critical parameters for arterial stiffness diagnosis. The values of $\Delta t_{DVP}$ and $AI_r$ are calculated as 296 ms and 53.3%, respectively, which are normal for a healthy person[86]. Heart rate variability (HRV) is the fluctuation in the time intervals between adjacent heartbeats. HRV has been proposed as an important indicator of cardiovascular illness[77], such as coronary artery disease and ischemic heart disease. To analyze the HRV, the peak-to-peak intervals were extracted and plotted in FIG. 5d. Using a time-domain method, the standard deviation of the beat-to-beat intervals (SDNN), the HRV was obtained as 27.69 ms (standard deviation) with a mean interval of 861.42 ms (using Kubios HRV analysis software), which falls in the normal range for healthy persons. The demonstrated capability of sensing such small-scale physiological mechanical signals in a self-powered manner, along with the biocompatibility, biodegradability, and low-cost fabrication of PVA materials, manifests the potential of PVA-based triboelectric devices for broader applications in biomedical fields.

In summary, this disclosure has presented the holistic engineering and systematic characterization of the impact of the molecular and ionic fillers on PVA blends' triboelectric performance, through revealing and understanding the interactions between the constituent materials and the structure-property-performance relations. Leveraging the high mechanical deformability and biocompatibility of the constituent materials, the triboelectric devices built with optimized PVA-gelatin composite films exhibit stable and robust triboelectricity outputs. Such wearable devices are capable of detecting the imperceptible degree of skin deformation induced by human pulse and capture the cardiovascular information encoded in the pulse signals with high fidelity. The gained fundamental understanding and demonstrated capabilities are expected to enable the rational design and holistic engineering of novel materials for more capable biocompatible triboelectric devices that can continuously monitor vital physiological signals for self-powered health diagnostics and therapeutics.

What is claimed is:
1. A triboelectric nanogenerator comprising:
a polyvinyl alcohol (PVA)-based biocompatible polymer, wherein the polyvinyl alcohol-based biocompatible polymer comprises a blending product of a mixture comprising a polyvinyl alcohol, a gelatin, and a salt, wherein the gelatin is provided in an amount effective to disrupt PVA crystalline domains;

a friction layer including a material more negative in a triboelectric series than the PVA-based biocompatible polymer; and metal electrodes coupling the polyvinyl alcohol (PVA)-based biocompatible polymer and the friction layer, and when the polyvinyl alcohol (PVA)-based biocompatible polymer is brought into contact with the friction layer, the difference from triboelectric polarities on the polyvinyl alcohol (PVA)-based biocompatible polymer and the friction layer leads to electrons flowing between the polyvinyl alcohol (PVA)-based biocompatible polymer and the friction layer;

wherein a concentration of the gelatin and the salt are provided to tune both interfacial polarization and ionic polarization so as to increase a dielectric constant of the PVA blend relative to pure PVA.

2. The triboelectric nanogenerator of claim 1, wherein the polyvinyl alcohol (PVA)-based biocompatible polymer comprises a blending product of a mixture comprising the polyvinyl alcohol, the gelatin, and the salt, wherein the salt comprises NaCl, KCl, or a combination thereof, and wherein the weight percentage of the salt is 0.5-1.3 wt. % of the total weight of the polyvinyl alcohol (PVA)-based biocompatible polymer, and the salt forms complexes with hydroxyl groups of PVA that reduce hydrogen-bond density and increase dipolar reorientation mobility.

3. The triboelectric nanogenerator of claim 1, wherein the polyvinyl alcohol (PVA)-based biocompatible polymer comprises 1-20 wt. % of the gelatin.

4. The triboelectric nanogenerator of claim 1, wherein the polyvinyl alcohol (PVA)-based biocompatible polymer is a substantially transparent film.

5. The triboelectric nanogenerator of claim 1, wherein the molecular weight of the polyvinyl alcohol is 100,000 to 250,000, and the molecular weight of the gelatin is 10,000 to 150,000.

6. The triboelectric nanogenerator of claim 1, wherein the polyvinyl alcohol (PVA)-based biocompatible polymer is a neutral material with pH range of 6.5-7.5.

7. The triboelectric nanogenerator of claim 6, wherein the polyvinyl alcohol (PVA)-based biocompatible polymer is a neutral material with pH value of about 7.

8. The triboelectric nanogenerator of claim 1, wherein the polyvinyl alcohol (PVA)-based biocompatible polymer has a dielectric constant range of 8-20.

9. The triboelectric nanogenerator of claim 1, wherein the friction layer comprises polyimide, polytetrafluoroethylene, polydimethylsiloxane, polyvinyl chloride, polypropylene (PP), or a metal.

10. The triboelectric nanogenerator of claim 1, wherein the PVA blend is processed to yield a crystalline grain size smaller than that of pure PVA, thereby increasing interfacial polarization area.

11. The triboelectric nanogenerator of claim 1, wherein a coil size of the PVA blend is adjusted by controlling at least one of:

gelatin loading to produce a maximum coil size at an intermediate concentration;

pH to maximize coil size at about pH 7; and cation type and concentration to control chain entanglement density.

12. The triboelectric nanogenerator of claim 1, wherein the triboelectric nanogenerator is adhered to skin and generates output signals in response to imperceptible skin deformations, the signals being processed to produce cardiovascular diagnostic indices.

\* \* \* \* \*